United States Patent [19]
Raible

[11] Patent Number: 5,270,005
[45] Date of Patent: Dec. 14, 1993

[54] EXTRACORPOREAL BLOOD OXYGENATION SYSTEM INCORPORATING INTEGRATED RESERVOIR-MEMBRANE OXYGENERATOR-HEAT EXCHANGER AND PUMP ASSEMBLY

[75] Inventor: Donald A. Raible, Santa Ana, Calif.

[73] Assignee: Baxter International Inc., Deerfield, Ill.

[21] Appl. No.: 906,900

[22] Filed: Jun. 29, 1992

Related U.S. Application Data

[63] Continuation-in-part of Ser. No. 783,712, Oct. 24, 1991, abandoned, and a continuation of Ser. No. 579,164, Sep. 7, 1990, abandoned.

[51] Int. Cl.$^5$ .................. A61M 1/18; B01D 19/00; B01D 61/00
[52] U.S. Cl. .................. 422/46; 422/48; 210/645; 210/175; 210/195.2; 210/198.1; 210/188; 261/DIG. 28; 128/DIG. 3; 604/4
[58] Field of Search .................. 422/46, 48, 45; 604/4; 128/DIG. 3; 261/DIG. 28; 210/175, 188, 195.2, 198.1, 321.62, 645, 646, 647, 929

[56] References Cited

U.S. PATENT DOCUMENTS

| | | | |
|---|---|---|---|
| 3,946,731 | 3/1976 | Lichtenstein | 128/DIG. 3 |
| 4,014,329 | 3/1977 | Welch et al. | 604/4 |
| 4,061,470 | 12/1977 | Leonard | 128/DIG. 3 |
| 4,073,622 | 2/1978 | Luppi | 261/DIG. 28 |
| 4,424,190 | 1/1984 | Mather, III et al. | 422/46 |
| 4,650,457 | 3/1987 | Morioka et al. | 128/DIG. 3 |
| 4,698,207 | 10/1987 | Bringham et al. | 422/46 |
| 4,818,490 | 4/1989 | Carson et al. | 422/46 |
| 4,828,543 | 5/1989 | Weiss et al. | 422/45 |
| 4,867,738 | 9/1989 | Mintz | 604/4 |
| 4,876,066 | 10/1989 | Bringham et al. | 422/46 |
| 4,886,487 | 12/1989 | Solem et al. | 604/5 |
| 4,902,476 | 2/1990 | Gordon et al. | 422/46 |
| 4,936,759 | 6/1990 | Clausen et al. | 128/DIG. 3 |
| 5,034,188 | 7/1991 | Nakanishi et al. | 422/46 |
| 5,039,430 | 8/1991 | Corey, Jr. | 210/188 |
| 5,124,127 | 6/1992 | Jones et al. | 422/46 |
| 5,152,964 | 10/1992 | Leonard | 128/DIG. 3 |

FOREIGN PATENT DOCUMENTS

| | | | |
|---|---|---|---|
| 0320815A | 6/1989 | European Pat. Off. | 261/DIG. 28 |
| 1437493 | 5/1976 | France | 422/48 |
| 22107976 | 6/1989 | United Kingdom | 261/DIG. 28 |

Primary Examiner—James C. Housel
Assistant Examiner—T. A. Trembley
Attorney, Agent, or Firm—Raymond Sun

[57] ABSTRACT

An extracorporeal blood oxygenation system comprising an integral blood processing unit having a blood reservoir/oxygenator/heat exchanger/pump and pump motor and a remote control console connectable to the integral blood processing unit by way of non-blood containing connections such as electrical cable or the like.

37 Claims, 6 Drawing Sheets

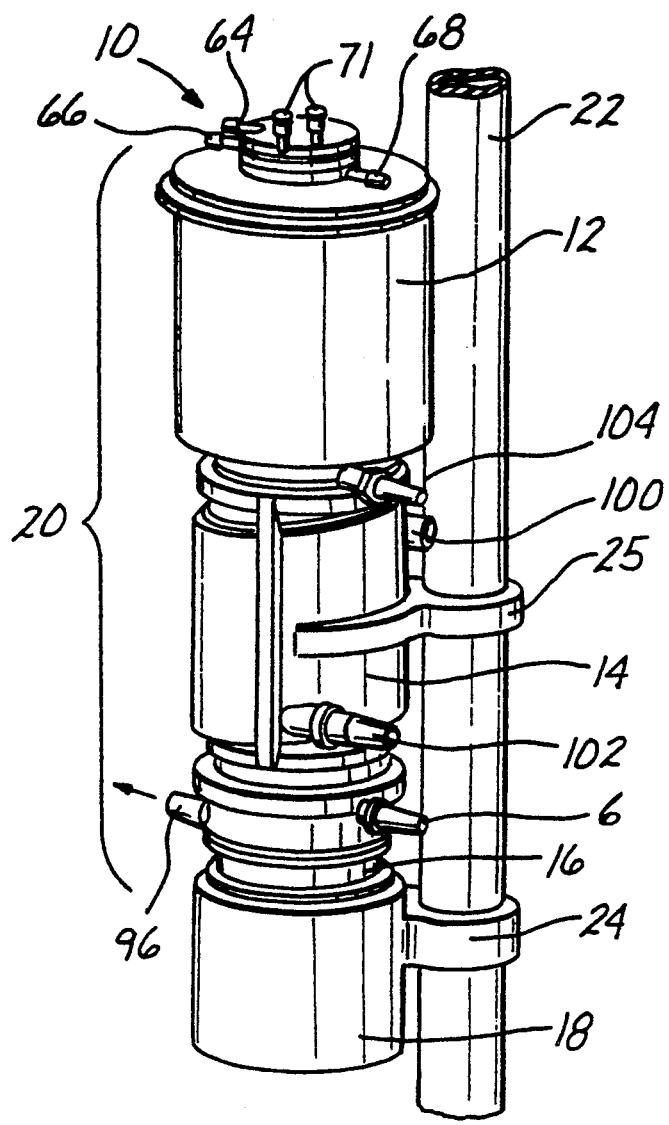
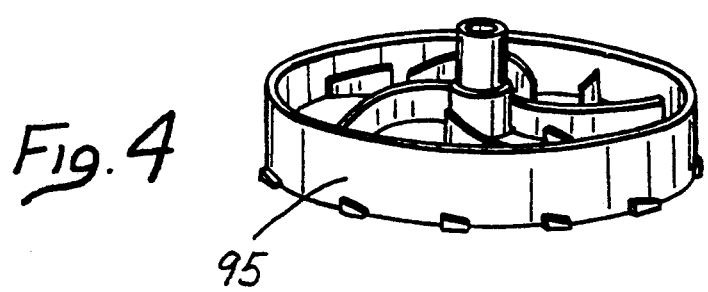

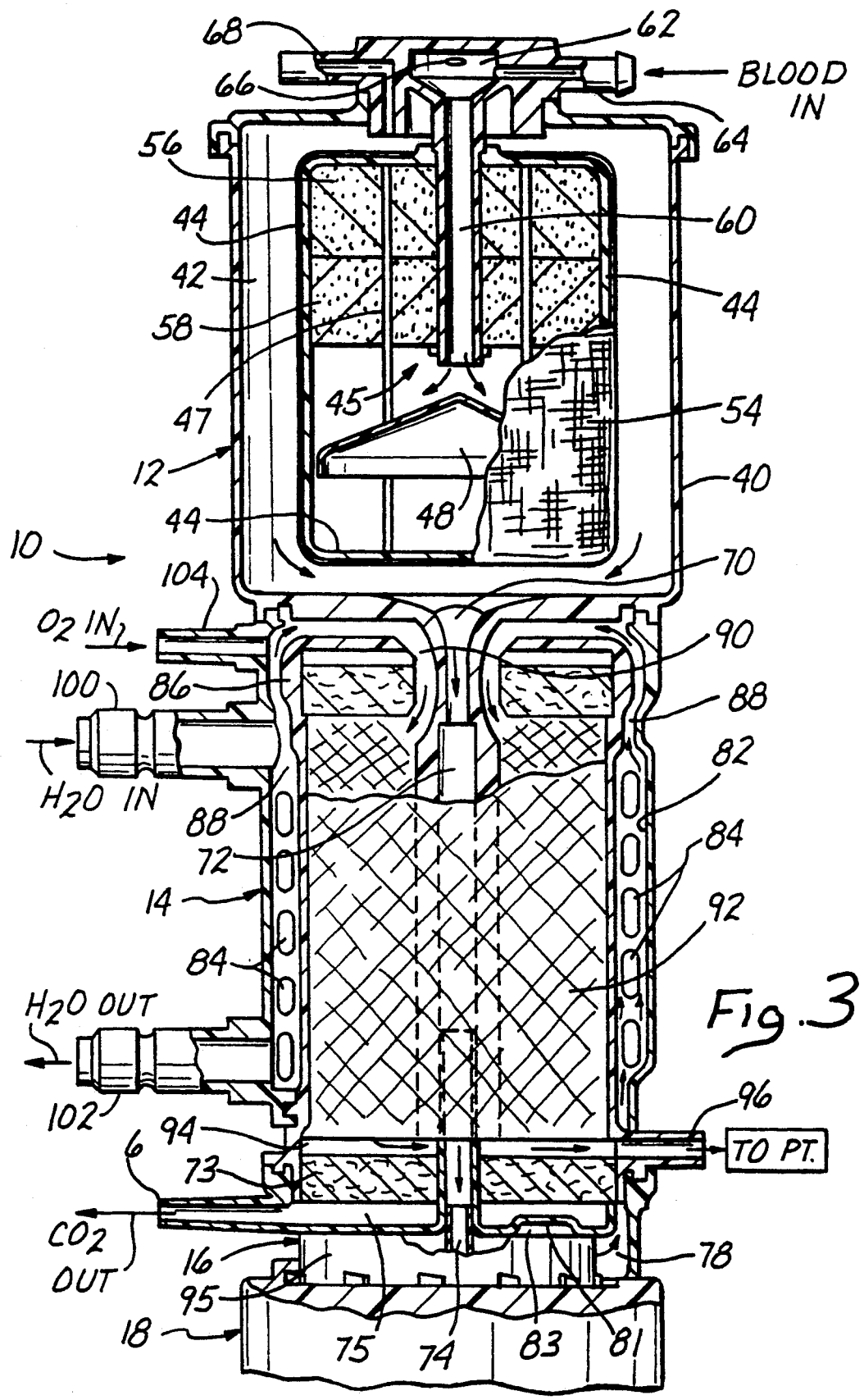

EXTRACORPOREAL BLOOD OXYGENATION SYSTEM INCORPORATING INTEGRATED RESERVOIR-MEMBRANE OXYGENERATOR-HEAT EXCHANGER AND PUMP ASSEMBLY

RELATED CASES

This application is a continuation-in-part of U.S. application Ser. No. 07/783,712, filed on Oct. 24, 1991, which is a continuation of U.S. application Ser. No 07/579,164, filed on Sep. 7, 1990, both of which are abandoned.

FIELD OF THE INVENTION

The present invention pertains generally to medical equipment and more particularly to an extracorporeal blood oxygenation system.

BACKGROUND OF THE INVENTION

Numerous extracorporeal blood oxygenation systems have been devised for purposes of pumping and oxygenating a patient's blood during cardiovascular surgery and/or other situations wherein the normal physiological functioning of the heart and lungs is interrupted or impaired.

Typical blood oxygenation systems of the prior art comprise four major components—(a) a venous reservoir, (b) a heat exchanger, (c) an oxygenator and (d) a blood pump. The "blood pump" portion of the system usually consists of a disposable peristaltic pump mounted directly upon a relatively large permanent motor drive. Some of the prior art blood oxygenation systems, such as that described in U.S. Pat. No. 4,698,207 (Bringham, et al.), have incorporated an integrated assembly comprising the (a) venous reservoir, (b) heat exchanger and (c) oxygenator components of the system. Such integral assembly may be located very close to the body of the patient. However, even when such integral venous reservoir/heat exchanger/oxygenator assembly is employed, it is still necessary to fluidly connect such integral assembly to a remotely positioned pump/control console so that blood may be circulated to the remotely positioned pump/control console wherein the pumping apparatus and system controls are housed.

In most cardiothoracic surgical procedures wherein extracorporeal blood oxygenation is employed, the crowded condition around the operating table generally precludes positioning the large pump/control console at a location immediately adjacent or close to the operating table. Thus, the pump/control console must be positioned some distance away from the table and lengthy blood-filled tubes must be run to and from the console to permit circulation of blood through the pumping apparatus housed in the pump/control console. The relatively long blood-filled tubes running to and from the pump/control console substantially increase the overall volume of the patient's blood which must be maintained in the extracorporeal circuit at any given point in time. Such increase in the length of the blood tubing, and the overall volume of blood in the extracorporeal circuit is undesirable for several reasons. First, it increases the amount of priming fluid (e.g. saline) deployed within the system and subsequently mixed with the patient's blood. Second, such increase in the volume of blood within the extracorporeal circuit will increase the volume of blood and/or blood products which must be administered by transfusion during the operative procedure. Additionally, such increase in the length of the tubing will substantially increase the amount of nonphysiological matter with which the blood comes in contact as it travels through the extracorporeal oxygenation system, thereby heightening the potential for mechanical, chemical and/or immunoloreactive damage to the formed and nonformed elements of the blood.

In view of the foregoing shortcomings of the prior art blood oxygenation systems, there exists a need for a blood oxygenation system which incorporates an integral assembly comprising (a) venous reservoir, (b) oxygenator, (c) heat exchanger and (d) pump, all of which may be positioned directly adjacent or close to the patient so as to eliminate the need for circulation of the patient's blood to a separate pumping device located in the remotely located pump/control console.

SUMMARY OF THE INVENTION

The present invention overcomes some or all of the problems of the prior art by providing a blood oxygenation system having an integral blood processing and oxygenation assembly which includes an integral pumping device, thereby eliminating the need for circulation of blood to a remotely located pump/control console.

In accordance with the invention, there is provided an integral blood processing unit comprising a blood reservoir component, a blood oxygenator/heat exchanger component, a pump component and a pump motor drive component. The blood reservoir component, oxygenator/heat exchanger component and pump component may be formed as a unitary disposable structure which is directly mountable on a reusable pump drive motor. The pump drive motor may be a relatively permanent structure which need not be disposable or sterilizable, as blood does not normally contact the pump drive motor during routine operation of the system.

Further in accordance with the invention, the blood reservoir, oxygenator/heat exchanger, pump and drive motor components of the system may be positioned in a generally vertical, stacked array so as to form a generally elongate structure attachable to a vertical pole or other support member. The vertical pole or other support member may be conveniently positioned beneath or adjacent to an operating table so that the integral blood oxygenation system may be positioned near the upper body of the patient. An aperture or passageway may be formed in the operating table to permit convenient passage of blood tubing therethrough, so as to circulate blood from the patient to the integral blood oxygenator assembly positioned beneath the operating table.

Still further in accordance with the invention, the pump component of the assembly may comprise any usable type of pump such as a peristaltic pump, ventricular pump, axial pump or centrifugal pump.

Still further in accordance with the invention, the pump motor drive may comprise a "motor drive base" sized and configured to receive the pump component of the assembly thereon and operative to engage and operate the pump assembly. In one embodiment, a centrifugal pump having a magnetic impeller is disposable on top of a motor drive base which incorporates a rotatable magnet therewithin, such that the rotatable magnet will operatively engage and rotate the magnetic impeller positioned within the centrifugal pump. In another embodiment, an axial pump having impeller rods is also disposable on top of the motor drive base such that the impeller rods are rotated by mechanical coupling of a pump shaft to the motor shaft. In yet another embodiment, a centrifugal pump having an impeller is disposable on top of the oxygenator/heat exchanger and below the blood reservoir, with the impeller rotated by means of a shaft extending from the motor drive base through a hollow bore in the oxygenator/heat exhanger. In a further embodiment, the axial pump may be located above the oxygenator/heat exchanger and below the blood reservoir, with the impeller rods rotated by mechanical coupling of a pump shaft to a motor shaft extending from the motor drive base through a hollow bore in the oxygenator/heat exhanger.

Still further in accordance with the invention, the blood reservoir component may comprise either a hard shell or flexible bag-like reservoir component. Additionally, the reservoir component may be a simple venous return reservoir or it may be adapted to receive both venous return blood and cardiotomy blood. The blood reservoir component may incorporate one or more blood filtering elements as well as one or more blood defoaming elements.

Still further in accordance with the invention, there may be provided one or more television cameras positioned near the integral blood processing unit so as to transmit television pictures of at least a portion of the integral blood processing unit to a television monitor located on the separate control console. Such will permit a perfusionist stationed at the control console to continually view at least a portion of the integral blood processing unit, although said integral blood processing unit may be located outside of the normal visual range of the perfusionist.

Further aspects, objects and advantages of the present invention will become apparent to those skilled in the art upon reading and understanding the following detailed description and the accompanying drawings.

BRIEF DESCRIPTION OF THE DRAWINGS

FIG. 2 is a perspective view of the blood reservoir/heat exchanger/membrane oxygenator/pump assembly of FIG. 1 affixed to a vertical pole stand;

FIG. 3 is a longitudinal sectional view of a portion of the blood reservoir/heat exchanger/membrane oxygenator/pump assembly of FIG. 1 having a centrifugal pump with a magnetic impeller disposed on top of the motor drive base;

FIG. 4 is a perspective view of the impeller element of one presently preferred pump component of the present invention;

DETAILED DESCRIPTION OF THE PREFERRED EMBODIMENTS

The following detailed description and accompanying drawings are provided for purposes of illustrating and describing the embodiments of the present invention and are not intended to limit the scope of the invention in any way.

Figure 1:
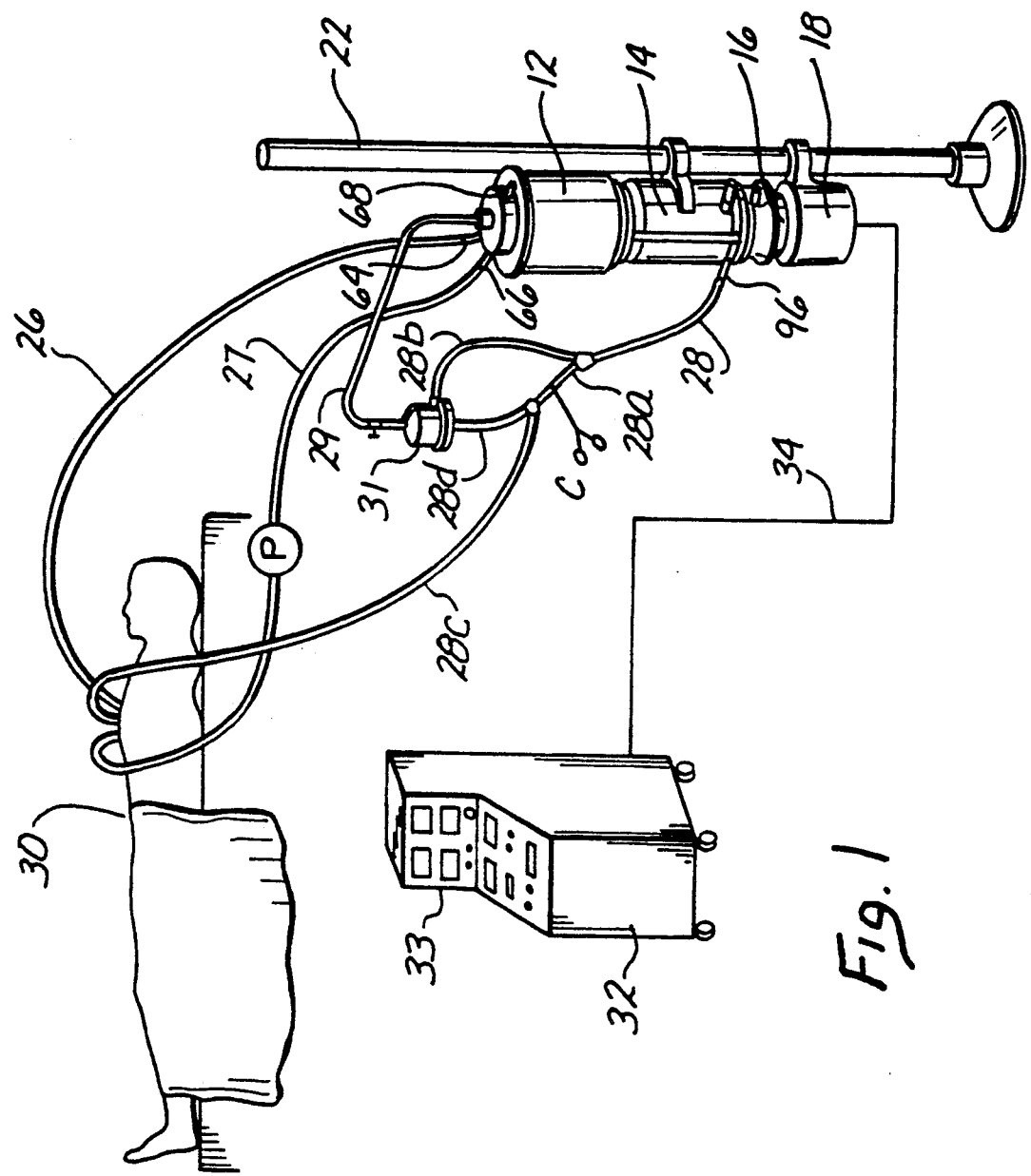
FIG. 1 is a perspective view of a first embodiment of a blood reservoir/heat exchanger/membrane oxygenator/pump assembly of the present invention connected to a human patient by way of flexible tubing and connected to a remote control console by way of electrical wiring.

As shown in FIGS. 1–3, the device according to one embodiment of the present invention comprises an integral blood reservoir/heat exchanger/membrane oxygenator/pump assembly 10. The assembly 10 comprises a combination venous/cardiotomy reservoir component 12, a membrane oxygenator/heat exchanger component 14, a pump component 16 and a motor drive base 18. In the embodiment shown, three of the components—namely the reservoir 12, oxygenator/heat exchanger 14 and pump 16 components, are interconnected to form a substantially unitary upper unit 20 which is directly mountable on the reusable, permanent motor drive base 18. The components of the upper unit 20 are preferably formed of plastic materials which may be sterilized by ethylene oxide or by other suitable chemical sterilants or radiation or other sterilization methods. The motor drive base 18, on the other hand, may be formed of metal, plastic or any other material and generally need not be subjected to sterilization as blood does not come in contact with the motor drive base 18 during normal operation of the system. The motor drive base 18 is operatively engageable with or connectable to the underside of the pump component 16 of the upper unit 20 so as to drive the pump 16 during operation of the system.

The integral blood reservoir/heat exchanger/ oxygenator/pump assembly 10 of the present invention is preferably sized and configured to be positionable immediately beneath or adjacent an operating table or patient treatment table. In the preferred embodiment shown, the upper unit 20 and motor drive base 18 are separately attachable to a vertical pole stand 22 or other support member. It will be appreciated that the vertical pole stand 22 or support member may actually be incorporated into the structure of the operating table, preferably beneath the head of the table so that the assembly 10 may be conveniently positioned at a location directly below the upper body of the patient. For example, a first pole engagement member 24 or clamp extends laterally from the body of the motor drive base 18 while a second pole engagement member 25 or clamp extends laterally from the upper unit 20. The pole engagement members 24, 25 are sized and configured to concomitantly hold the upper unit 20 comprising the integral reservoir 12, heat exchanger-oxygenator 14 and pump 16 in a vertically juxtaposed, directly contacting and operationally engaged position relative to the motor drive base 18, as shown.

A venous blood return line 26 is connected between the patient and the reservoir 12, and serves to shunt venous blood from the vena cava of the patient to the venous blood inlet port 64 of the reservoir component 12. A cardiotomy blood line 27 is fluidly connected between the patient and the reservoir 12, and serves to shunt aspirated cardiotomy blood from the operative sight to the cardiotomy blood inlet port 66 of the reservoir component 12. Available wall suction or a dedicated suction pump P may be employed to effect suctioning of the cardiotomy blood through line 27.

A network of arterial blood return lines 28, 28a, 28b, 28c, 28d and a secondary blood filter 31 are connected to the arterial blood outlet port 96 of the oxygenator/heat exchanger component 14 as shown. The distal end of line 28c is fluidly connected to the patient's aorta to infuse oxygenated blood exiting the oxygenator 14 into the patient's vasculature. A recirculation tube 29 may fluidly connect the interior of the secondary blood filter 31 to one of the two (2) inlet ports 71 formed in the roof or top portion of mixing chamber 62. Thus, when clamp C is closed, the returning arterial blood will be diverted through filter 31 and back into the reservoir component 12 for recirculation through the assembly 10.

A control console 32 may be connected to the integral reservoir/heat exchanger/membrane oxygenator/pump assembly 10 by way of electrical line, cable, radio waves, or other non-blood-transporting connection. Because it is connected to the integral assembly 10 only by way of a nonfluid connection, such as an electrical line 34, it is feasible that the control/monitoring console 32 be located some distance (e.g. 10-30 feet) away from the assembly 10 while still providing routine electronic control and monitoring of the standard operational variables and parameters of the blood oxygenation system from such remote location.

The control/monitoring console 32 is connected by line, electrical cable 34 or other non-blood transporting connection to various sensor devices and control devices located on or adjacent the integral assembly. Typically, the control/monitoring console will provide means for enabling the perfusionist to control various operational variables such as pump speed, motor speed, blood flow rate and arterial pressure. Additionally, the control monitoring console 32 of the present invention will preferably incorporate a CRT or television screen monitor 33 or other display to display other operational variables such as; arterial and venous blood temperatures, systemic arterial pressure, $P_{O_2}$, $P_{CO_2}$, oxygen saturation, activated clotting times and/or other indicators of blood coagulation activity, particulate counts and/or other data which may be of interest to the perfusionist during the operative procedure. Additionally, since the control/monitoring console 32 of the present invention is able to be stationed remotely from the integral assembly 10, one or more television cameras may be provided near the assembly 10 and connected to the television monitor 33 portion of the control/monitoring console to enable the perfusionist to view all or portions of the integral assembly from his/her position at the remote control/monitoring console. Such TV monitoring capability is particularly useful to enable the perfusionist to view the blood level in the reservoir 12 component during operation.

It is desirable that the integral reservoir/heat exchanger/oxygenator/pump assembly 10 be positioned as close to the patient as possible so as to minimize the length of blood lines 26 and 28, thereby decreasing the amount of blood which is circulated through the extracorporeal circuit at any given point in time. Because the assembly 10 of the present invention obviates the need for circulating the patient's blood to a remotely located pump/control console, the potential for over dilution or injury to the blood is minimized. Furthermore, because the control and monitoring console 32 used in conjunction with the present invention is connected to the assembly 10 only by way of electrical wires or other remote systems, such console 32 may be stationed a substantial distance (10-50 feet) away from the assembly 10, without the need for circulating the patient's blood over such a long distance and without extending blood filled tubes across the operating room floor as may present a trip hazard and as may act as an obstacle to routine movement of personnel about the operating room.

The integral assembly 10 may be positioned beneath the head of the operating table and the blood lines 26, 28 may be passed upwardly just adjacent the table. Alternatively, the blood lines 26, 28 may be passed upwardly through a passageway or aperture formed in the table near the patient's thorax. Such positioning of the device 10 and passage of the lines 26, 28 adjacent to the table or through a passageway or aperture formed in the table, will minimize the length of lines 26, 28, thereby requiring minimum priming volume. Such positioning will also serve to keep the lines 26, 28 in conveniently stowed positions whereat such lines 26, 28 are not likely to be inadvertently pulled, tugged, disrupted, stepped on, punctured or otherwise interfered with.

FIG. 3 is a longitudinal sectional view of the integral assembly 10, showing the operative internal components of a first embodiment of the present invention. In the embodiment shown, the blood reservoir component 12 comprises a hard shell reservoir adapted to receive, filter and collect both (a) venous return blood (i.e. blood shunted directly into the reservoir 12 from the vena cava of the patient) and (b) cardiotomy blood (i.e. blood aspirated from the thoracic cavity or elsewhere near the operative site). The blood reservoir component 12 comprises a hard outer shell 40, preferably made of clear thermoplastic such as polycarbonate. The hard outer shell 40 of the reservoir component 12 defines an open reservoir chamber 42 therewithin. A support cage 47 is attached to a frusto-conical or generally conical baffle structure 48 and a microscreen filter element 44 is disposed upon and supported by the support cage 47. The microscreen filter element 44 comprises a fine mesh screen of relatively physiologically inert material having an average pore size of 50-100 microns. The microscreen filter element 44 is configured to define therewithin a blood receiving inner compartment 45.

A polyester mesh sock 54 is disposed fully about the outer surface of the microscreen filter element 44 and about the generally conical or frusto-conical baffle structure 48, as shown. The polyester mesh sock 54 has an average pore size of about 100 microns.

One or more defoamer rings 56, 58 are disposed within the upper portion of the blood receiving inner compartment 45 defined within microscreen filter element 44. Such defoamer rings 56, 58 are sized and configured to fit within the blood receiving inner compartment 45 such that the defoamer rings generally occupy the upper region of such compartment 45, from the inner surface of the microscreen filter element 44 to the outer surfaces of the blood inlet tube 60. Such defoamer rings 56, 58 are formed of porous (e.g. open cell) flexible foam material, such as open cell polyurethane foam. One or more of the defoamer rings 56, 58 may be coated with, impregnated with, or otherwise contain, a defoaming chemical substance such as silicon oxide or simethicone or other antifoam agent. It is preferable that the upper defoamer ring 56 be made of foam material which is more porous than the lower defoamer ring 58. For example, the upper defoamer ring may be made of material having approximately 5-20 pores per square inch, and preferably about 20 pores per square inch, while the lower defoamer ring 58 may be made of material having about 40-60 pores per square inch, and preferably about 50 pores per square inch. The defoamer rings 56, 58 have central apertures formed therein, such central apertures being sized and configured to fit snugly about vertical blood inlet tube 60. The vertical blood inlet tube 60 is fluidly connected to and extends vertically downward from a mixing chamber 62 positioned at the top end thereof. A venous blood inlet 64 and a cardiotomy blood inlet 66 both lead into mixing chamber 62. By such arrangement, the incoming venous blood and cardiotomy blood may be simultaneously infused into the mixing chamber 62. The combined venous and cardiotomy blood will then undergo subsequent drainage down vertical tube 60 into the blood receiving inner compartment 45 of the filter element 44. Blood exiting the bottom end of the vertical tube 60 may impinge against the generally conical upward projection of baffle structure 48, thereby causing the blood flow to be separated and directed outwardly in lateral directions. The blood will subsequently pass outwardly through the microscreen element 44 and polyester sock 54. After passing through the microscreen element 44 and polyester sock 54, the blood will collect in the reservoir chamber 42. Such passage of the blood through the microscreen element 44 and polyester sock 54 will substantially remove air bubbles, emboli, foreign matter and other materials entrained within the blood.

A vent tube 68 opens through the top of the hard shell 40 of the reservoir component 12 so as to vent gas at least out of and preferably into and/or out of the chamber 42. Such vent tube 68 facilitates passage of ambient air into and out of the chamber 42 in response to variations in the liquid level within the chamber 42, thereby preventing the build up of negative and/or positive pressure therewithin. The microscreen element 44 and support cage 47 are configured to define a blood receiving inner compartment 45 within the microscreen element 44, such inner compartment 45 is specifically sized to receive inflow of cardiotomy and venous return blood at the normal operative inflow rates such that the level of blood therewithin will generally remain below the bottom edge of the lower defoamer ring 58. Thus, in routine operation, only surface foam or bubbles will rise high enough to come in contact with the lower defoamer ring 58.

An aperture 70 is formed in the floor or bottom wall of the rigid shell 40 so as to allow blood which has been filtered through the microscreen element 44 and polyester sock 54 and which has collected in chamber 42 to pass downwardly through central tube 72 through the center of the membrane oxygenator/heat exchanger component 14. After reaching the bottom of the central tube 72, the blood may pass into the central inlet 74 of the pump 16. The pump impeller 95 or other functional pumping device may thereafter propel and pump the blood upwardly through an internal blood flow passageway 78 which directly communicates with an annular heat exchange space 88, as shown in the arrows of FIG. 3. The heat exchange coil 84 is disposed adjacent the inner surface of the outer shell 82. A rigid inner shell 86 is formed within the outer shell 82, just inboard of the heat exchange coil 84. Thus, the heat exchange space 88 is defined between the inner surface of the outer hard shell 82 and the outer surface of the inner hard shell 86, through which blood may circulate. The space 88 is configured so that blood from the passageway 78 may pass upwardly through the space 88 and may subsequently flow from space 88 into passageway 90. The blood may then flow downwardly through the passageway 90 and subsequently circulate downwardly about a mutiplicity of tubular hollow fiber membranes 92 disposed within the cavity formed between the inner surface of the inner hard shell 86 and the outer surface of the central tube 72. The partial pressure of oxygen ($pO_2$) within the blood will increase as oxygen diffuses outwardly from the inner lumens of the hollow fiber membranes through the walls of the hollow fiber membranes and passes into the blood. The concentration of oxygen within the gas passing through the central lumen of the hollow fibers and/or the pressure of oxygen-containing gas within the hollow fibers may be controlled and varied in accordance with routine blood oxygenation system operating techniques and procedures.

The hollow fiber membranes 92 comprise tubular, gas permeable hollow fiber membranes of the type well known in the art and which are routinely used in membrane oxygenation systems of this type.

Generally, the hollow fiber membranes 92 act as conduits for the flow of oxygen. Each individual hollow fiber is of tube-like configuration and is formed of microporous membrane material preferably having pores of about 350 to 380 microns formed therein, which permits some of the oxygen passing through the lumen of the hollow fiber membrane to flow through the microporous membrane to the outer surface of the hollow fiber where the oxygen is taken up by blood circulating around the exterior of the hollow fiber. Carbon dioxide from the blood also passes through the membrane, in the opposite direction, and become mixed with the gas flowing through the hollow fibers. The bottom ends of the lumens of the hollow fiber membranes 92 are fluidly connected to collection space 75 such that $CO_2$ containing gas passing out of the bottom ends of the lumens of the hollow fiber membranes 92 will flow into gas collection space 75 and may subsequently pass out of gas outlet port 106.

A specific construction and manner in which the hollow fiber membranes 92, attendant mounting structures and the heat exchanger 84 are operatively and functionally incorporated into the oxygenator/heat exchanger component 14 of the present invention is fully described in U.S. patent application Ser. No. 428,270 entitled BLOOD OXYGENATION SYSTEM, filed Oct. 26, 1989, and now pending the entire specification and drawings of which are expressly incorporated herein by reference. The oxygenator/heat exchanger device described in application Ser. No. 428,270 is similar to and may be interchanged with the heat exchanger/oxygenator component 14 shown in FIGS. 1-3.

A blood collection space 94 is fluidly connected to the space surrounding the outer surfaces of the hollow fiber membranes 92 such that blood that has flowed downwardly around the hollow fibers may pass into collection space 94, whereafter such oxygenated blood may pass outwardly through outlet port 96 as arterial blood (A).

It will be appreciated that the pump component 16 of the present invention may comprise any type of pumping apparatus capable of pumping blood from the bottom of tube 72 back upwardly through the heat exchanger/oxygenator component 14. In the preferred embodiment shown, the pump 16 comprises a centrifugal type pump such as that available under Catalog Number 2100-CP from Aires Medical, 12 Elizabeth Drive, Chelmsford, Mass. 01824. It will be appreciated that the assembly 10 may alternatively incorporate other designs or makes of centrifugal pumps as well as various other types of pumps such as a ventricular pump, an axial pump, or a peristaltic pump.

In embodiments and applications wherein a peristaltic pump is employed, the motor drive base 18 may incorporate a plurality of rollers or peristaltic tubing compressors mounted on the upper side of the motor drive base 18 so as to effect the desired peristaltic compression of one or more compressible tubes mounted on exposed regions of the pump head.

In embodiments and applications wherein a ventricular type of pump is employed, the motor drive unit may be fitted with one or more mechanical thrust arms capable of engaging and repeatedly triggering, actuating or compressing a ventricular type pumping mechanism.

The motor drive base 18 may comprise any suitable motor capable of driving the pump. In the embodiment shown the motor drive base 18 is of the type marketed under Catalog Number 2100-MD by Aires Medical, 12 Elizabeth Drive, Chelmsford, Mass. 01824. In this preferred embodiment, the motor drive base 18 incorporates a rotating electromagnet which functions to magnetically couple and rotate the plastic pump impeller 95, which has a magnet embedded or molded therein. It will be appreciated, however, that the motor drive base 18 may also function by frictionally engaging the pump impeller 95 or otherwise mechanically interfacing with the pump 16 so as to effect the desired movement and operation of the pump 16.

The pump 16 may be engageable with the motor drive base 18 by any suitable means including direct surface to surface engagement or a screw threaded or bayonet type of engagement or through mechanical coupling.

Figure 5:
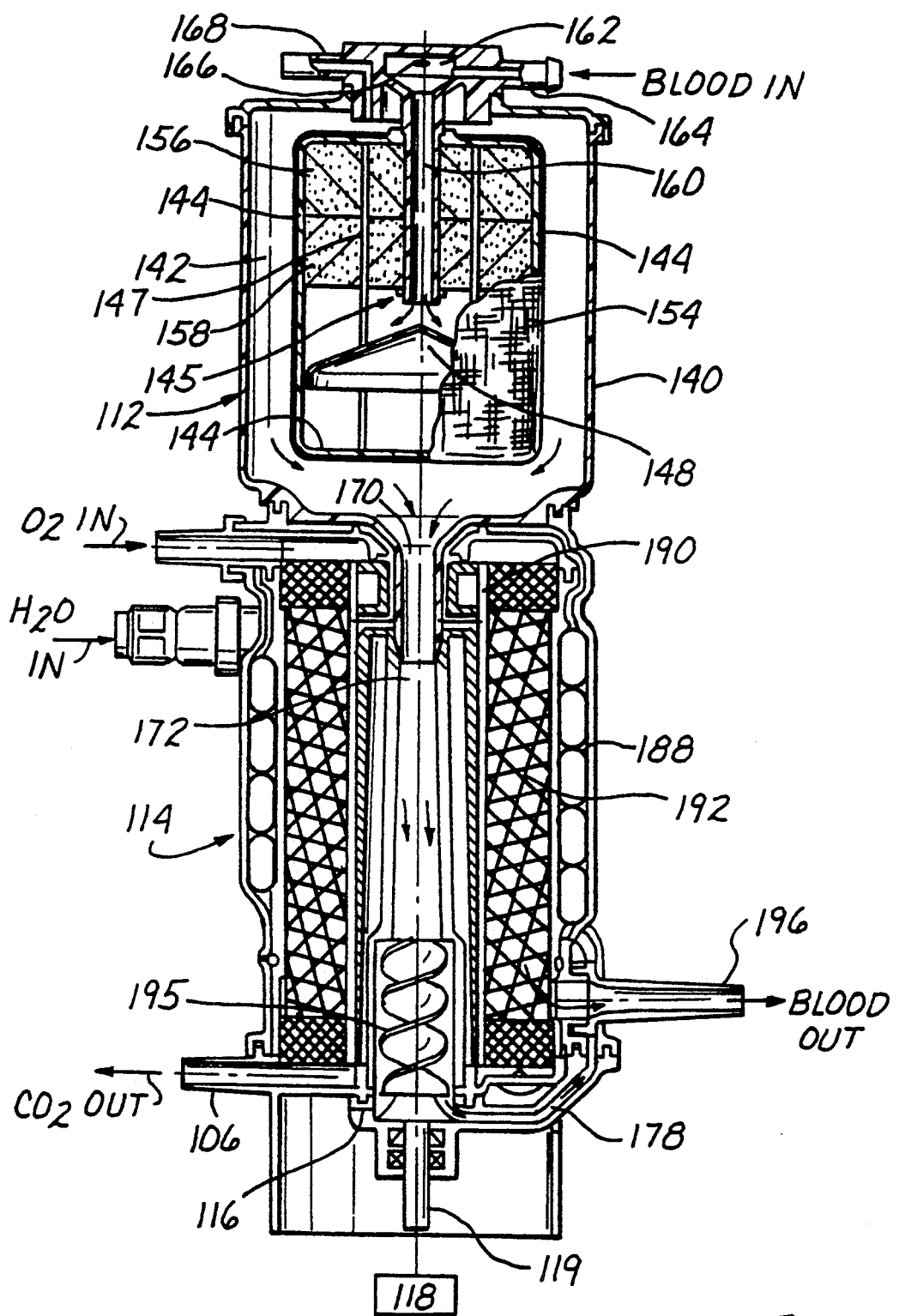
FIG. 5 is a longitudinal sectional view of a portion of a second embodiment of the blood reservoir/heat exchanger/membrane oxygenator/pump assembly of the present invention having an axial pump with an impeller mechanically coupled to the drive motor and disposed on top of the motor drive base.

FIG. 5 is a second embodiment of the present invention in which an axial pump 116 is disposed on top of the motor drive base 118 by mechanically coupling a pump shaft 119 to the motor drive base 118. The structures of the reservoir component 112 and the oxygenator/heat exchanger unit 114 are otherwise identical to that of the reservoir component 12 and the oxygenator/heat exchanger unit 14, respectively, of the embodiment of FIG. 3, unless otherwise noted hereinbelow. Blood collected in the chamber 142 passes through the aperture 170 and the central tube 172 through the center of the oxygenator/heat exchanger unit 114. Upon reaching the bottom of the central tube 172, the blood is propelled and pumped by the impeller 195 of the axial pump 116 upwardly through an internal blood flow passageway 178 which directly communicates with heat exchange space 188, as shown in the arrows in FIG. 5. The blood circulates upwardly through the heat exchange space 188 and flows into passageway 190. The blood then flows downwardly through passageway 190 and circulates downwardly about the multiplicity of tubular hollow fiber membranes 192 and flows out through the outlet port 196. An example of the axial pump 116 is shown and described in U.S. Pat. No. 5,040,944 to Cook, issued on Aug. 20, 1991, the entire specification and drawings of which are expressly incorporated herein by reference.

Figure 6:
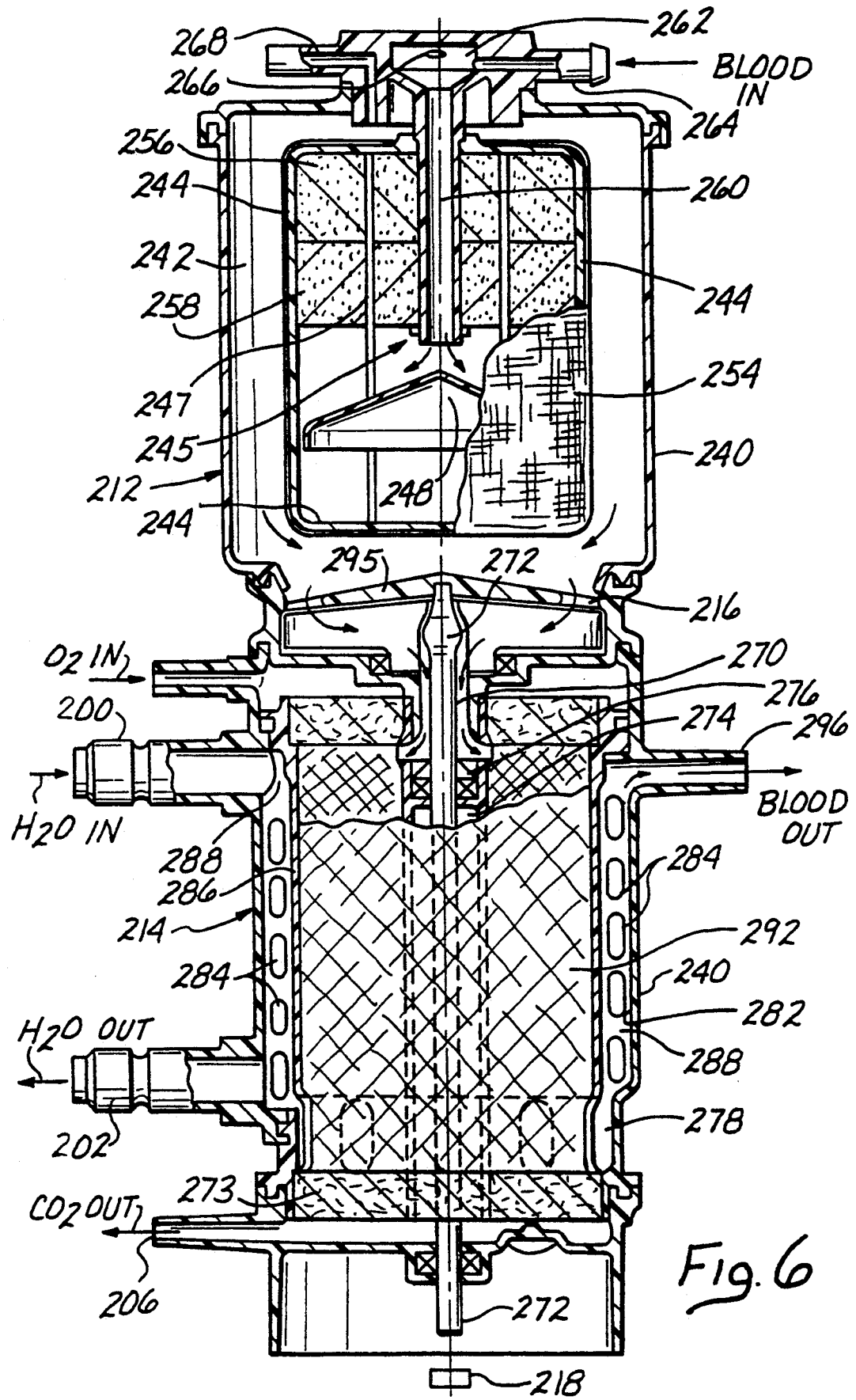
FIG. 6 is a longitudinal sectional view of a portion of a third embodiment of the blood reservoir/heat exchanger/membrane oxygenator/pump assembly of the present invention having a centrifugal pump having an impeller mechanically coupled to the drive motor and disposed on top of the oxygenator/heat exchanger and below the blood reservoir.

FIG. 6 is a longitudinal sectional view of a third embodiment of the present invention in which the centrifugal pump 216 is disposed between the oxygenator/heat exchanger unit 214 and the reservoir component 212. One end of a shaft 272 is connected to the motor drive base 218 and the other end extends through a hollow bore 274, a seal 276, and an aperture 270 to be connected to the pump 216. Rotation of the shaft 272 causes the pump impeller 295 to propel and pump blood collected in chamber 242 through aperture 270. The seal 276 prevents the passage of blood into the hollow bore 274 and instead directs the blood to circulate downwardly through the plurality of tubular hollow fiber membranes 292. Upon reaching the bottom of the tubular hollow fiber membranes 292, the blood enters and circulates upwardly through an internal blood flow passageway 278 and the heat exchange space 288, and exits through outlet port 296 as arterial blood.

Figure 7:
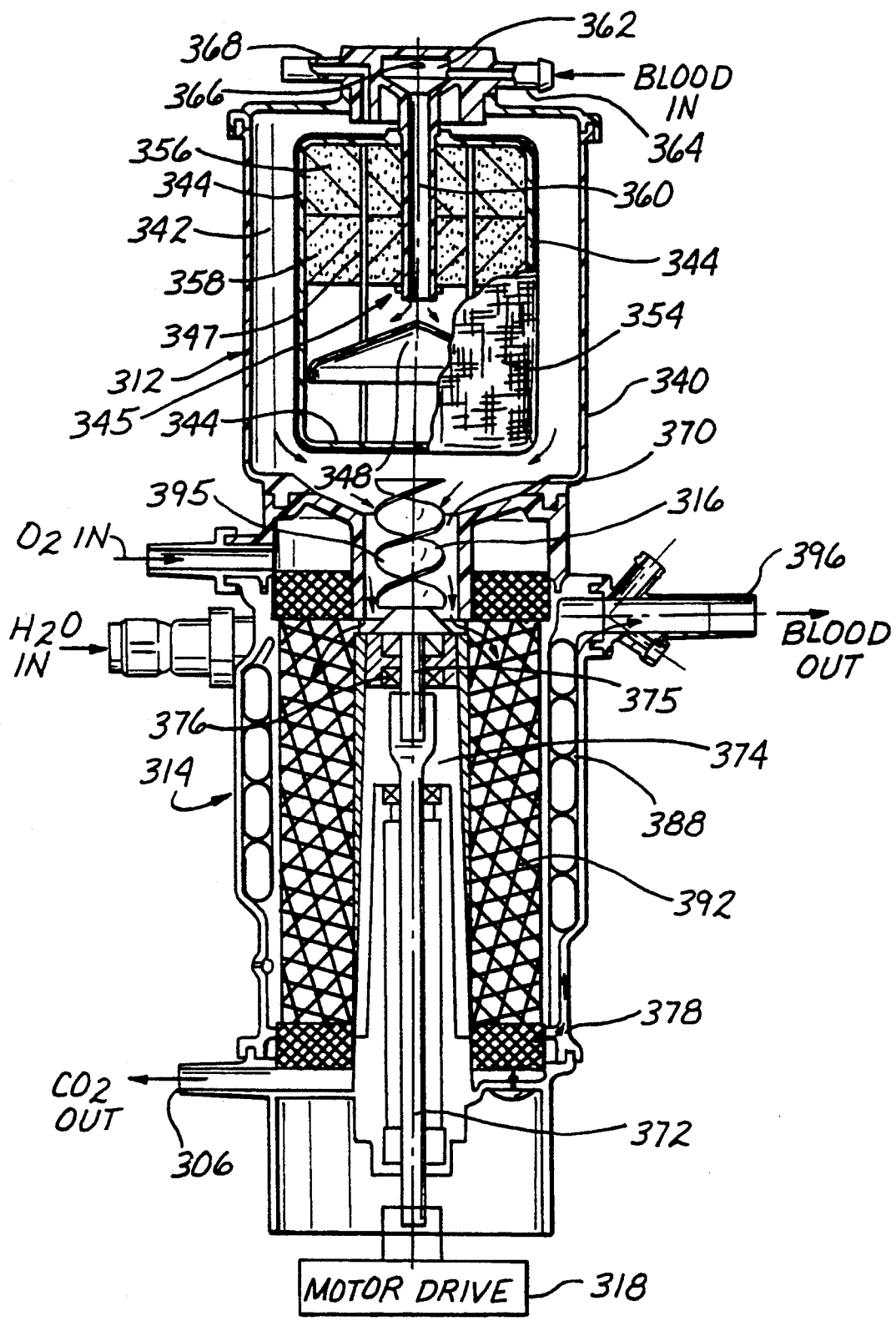
FIG. 7 is a longitudinal sectional view of a portion of a fourth embodiment of the blood reservoir/heat exchanger/membrane oxygenator/pump assembly of the present invention having an axial pump having an impeller mechanically coupled to the drive motor and disposed on top of the oxygenator/heat exchanger and below the blood reservoir.

FIG. 7 is a fourth embodiment of the present invention in which an axial pump 316 is disposed between the oxygenator/heat exchanger unit 314 and the reservoir component 312. One end of a drive shaft 372 is connected to the motor drive base 318 and the other end extends through a hollow bore 374 and is connected to a pump shaft 375 of the pump 316, which extends through a seal 376 and an aperture 370. Rotation of the drive shaft 372 and the pump shaft 375 causes the impellers 395 to propel and pump blood collected in chamber 342 through aperture 370. The seal 376 prevents the passage of blood into the hollow bore 374 and directs the blood to circulate downwardly through the plurality of tubular hollow fiber membranes 392. Upon reaching the bottom of the tubular hollow fiber membranes 392, the blood enters and circulates upwardly through an internal blood flow passageway 378 and the heat exchange space 388, and exits through outlet port 396 as arterial blood.

The provision of an integrated reservoir/heat exchanger/oxygenator/pump assembly eliminates the need for tubing lines which are typically required to connect the pump with the reservoir, oxygenator and heat exchanger units. This facilitates a reduction in line or tubing pressure, allows a smaller pump to be used, and also allows an oxygenator having higher differential pressure across it to be supported without the need for a larger pump. This also increases safety by eliminating the possibility of tube kinking which can cause a restriction in blood flow.

The elimination of tubing lines also allows the integrated assembly to effect pulsatile pumping, which improves the mixing of red cells among the hollow fibers for increased oxygen and carbon dioxide transfer. This occurs by pulsing the blood around the hollow fiber membranes which causes the red cells to come in contact with more of the membrane surface area.

The integrated assembly further allows for more predictable performance and therefore, safety, since the perfusionist cannot alter the relationship between the oxygenator, reservoir and blood pump, which is possible under systems that are currently available.

OPERATION OF THE PREFERRED EMBODIMENT

The embodiment shown in FIGS. 1-3 is routinely operated by initially placing a sterilized upper unit 20 on the vertical pole stand 22 such that the basal portion or underside of the pump component 16 operatively engages the motor drive base 18. The venous blood return tube 26 and cardiotomy blood return tube 27 are attached to venous blood inlet 64 and cardiotomy blood inlet 66 respectively. The network of oxygenated blood return tubes 28, 28a-d and the attendant blood filter 31 are attached to arterial blood outlet 96 of the assembly 10. Temperature control, water or other heat exchange medium is passed into water inlet 100, circulated through heat exchanger coil 84 and passed out of water outlet 102. It is preferable that a recirculating temperature control unit be utilized to circulate temperature controlled heat exchange medium through the heat exchange coil 84. In routine operation, the water or other liquid heat exchange medium will be varied between 26°-42° C. It is preferable that the heat exchange coil 84 be formed of stainless steel as stainless steel is known to exhibit thermal conductivity properties which are desirable in this heat exchange application.

An oxygen supply tube is connected to oxygen inlet 104 and a carbon dioxide vent tube is connected to carbon dioxide outlet 6. Oxygen or oxygen/room air mixture is passed into the inlet 104 such that the oxygen or oxygen/room air mixture flows through the lumens of hollow fibers 92 and subsequently out of carbon dioxide port 6. An antibacterial or microbiostatic filter may be positioned on inlet port 104 to remove potentially pathogenic organisms from the incoming oxygen or oxygen/room air mixture. One such filter which may be utilized for this purpose is the Bentley Laboratories, GF-10 Bidirectional Gas Filter manufactured by Baxter Healthcare Corp., Bentley Laboratories Division, Irvine, Calif.

After cardiopulmonary bypass has begun, a relatively constant flow of venous return blood will flow through venous return line 26 into venous blood inlet port 64 and into the mixing chamber 62 at the top of the reservoir component 12. Additionally, the aspirator pump P or wall suction may be actuated so as continually suction or aspirate cardiotomy blood from the operative site, through cardiotomy blood inlet line 27, and into the mixing chamber 62 through cardiotomy blood inlet port 66. The resultant mixture of venous return blood and cardiotomy blood will then descend downwardly, through vertical tube 60 into the blood receiving inner compartment 45. Blood flowing out of the bottom end of vertical tube 60 may impinge against the generally conical baffle structure 48, thereby causing the blood to undergo substantially even separation of flow in all lateral outward directions. The blood will subsequently flow outwardly through the microscreen element 44, through the surrounding polyester sock 54 and into the reservoir chamber 42.

Any blood foam or bubbles rising within the blood receiving inner compartment 45 will come in contact with at least one of the defoamer rings 56, 58. The defoamer rings will serve to chemically defoam and/or collectively filter out air bubbles and blood foam.

Because the rate of cardiotomy and venous return blood inflow typically varies, it is foreseeable that the level of blood within the reservoir chamber 42 will vary during normal operation. The open vent 68 formed at the top of reservoir chamber 42 will allow continual inflow and outflow of ambient air into and out of the chamber 42, thereby preventing any buildup of positive or negative pressure within the chamber 42 as a result of fluctuations in the level of blood contained therewithin.

The filtered blood contained within chamber 42 will undergo gravity drainage, at a relatively constant rate, through aperture 70 and downwardly through central tube 72 and into the central inlet 74 of pump 16. The pump impeller 95 will be continually rotated by the motor drive base 18 so as to pump blood entering the pump inlet 74 through passageway 78 to the heat exchanger portion of the heat exchanger/oxygenator component 14, in which the blood will flow around the convoluted portions of the heat exchanger coil 84 so as to undergo substantial temperature equilibration with the temperature of the heat exchange medium being circulated through the coils 84. After passing over the heat exchange coil 84, the blood will flow upwardly through space 88 and will subsequently drain downwardly over the hollow fiber membranes 92 disposed within a cavity defined between the inner surface of inner wall 86 and the outer surface of central tube 72. Oxygen flowing through the hollow fiber membranes 92 will diffuse outwardly so as to oxygenate the blood. Carbon dioxide given up by the blood will diffuse inwardly so as to mix with the residual gas flowing through the inner lumens of the hollow fiber membranes 92. The $CO_2$ containing residual gas will pass out of the bottoms of the hollow fiber membranes 92 and will be manifolded into lower space 75, just beneath the basal potting structure 73. The $CO_2$ containing residual gas will then pass out of gas outlet 6 and be vented into the atmosphere. A recessed pressure relief valve 81 is formed in a raised region of the bottom floor of residual gas collection chamber 75. In the event that the gas pressure exceeds a predetermined pressure limit the pressure relief valve 81 will allow excess gas pressure to vent into space 83. Space 83 will communicate with the atmosphere so as to provide for complete venting and escape of any gas which passes outwardly through pressure relief valve 81.

Blood passing downwardly over the outer surfaces of the hollow fiber membranes 92 becomes sufficiently oxygenated and loses sufficient carbon dioxide to be reinfused into the patient 30 as arterial blood. After passing downwardly over the hollow fiber membranes 92, the "arterial" blood enters space 94 and flows out of outlet port 96, through lines 28, 28a and 28c, into the aorta of the patient 30. Line 28b is normally clamped. If it is desired to pass the arterial blood through secondary blood filter 31, line 28a may be clamped and line 28b unclamped. Such will cause the arterial blood to pass through lines 28, 28b, filter 31, line 28d and line 28c prior to entering the patient's vasculature.

When the operative procedure has been completed, the flow of heat exchange medium into inlet 100 is terminated, the flow of oxygenated gas into inlet 104 is terminated, and the gas and heat exchange medium lines are disconnected therefrom. The blood lines 26, 27 and 28c are disconnected from the patient, the motor drive base 18 is deenergized or turned off and the upper unit 20 is disconnected from the motor drive base 18 and, along with all disposable blood soiled lines (26, 27, 28, 28a, 28b, 28c, 28d) is disposed of in a sanitary fashion.

Thereafter, the motor drive base 18 remains positioned on the vertical pole stand 22, ready to receive a subsequent disposable upper unit 20 and attendant lines 26, 27, 28, 28a, 28b, 28c, 28d for use with a subsequent patient.

It will be understood by one skilled in the art that the operating principles for the embodiment of FIGS. 1-3 are equally applicable to the embodiments of FIGS. 5, 6 and 7.

The foregoing description is intended to describe and illustrate a presently preferred embodiment of the invention only. It is probable that those of skill in the art will recognize various changes, modifications and substitutions which may be made to the above-described embodiment without departing from the spirit and scope of the invention. For example, a flexible bag-type venous reservoir may be used in place of the hard shell reservoir component 12 of the present invention. Such flexible bag type reservoir may be attached to the vertical pole 22 or other supporting member and directly connected to the inlet port 70 of the oxygenator/heat exchanger component 14. Thus, such alteration of the preferred embodiment is entirely foreseeable and intended to be within the scope of the invention and the following claims. Also, it will be appreciated that the reservoir component 12 of the assembly 10 need not necessarily incorporate both a cardiotomy reservoir and venous return reservoir. Indeed, a simple venous return reservoir may be used without any cardiotomy reservoir, or with a separate cardiotomy reservoir and defoamer unit as is known in the art.

What is claimed is:

1. A blood processing unit for extracorporeal blood oxygenation, said blood processing unit being connectable by non-blood transporting connection to a remote control console, the blood processing unit comprising:

an integral structure comprising (a) a blood reservoir, (b) a membrane oxygenator/heat exchanger formed integrally below the blood reservoir and comprising an outer shell, a first internal blood flow path centrally disposed therewithin, an annular heat exchange space provided adjacent the outer shell, a plurality of hollow fiber membranes provided between the first internal blood flow path and the annular heat exchange space and in fluid communication with the annular heat exchange space, and a blood outlet disposed in fluid communication with the plurality of hollow fiber membranes, (c) a pump attached below the membrane oxygenator/heat exchanger and fluidly connected to the blood reservoir to receive blood from the blood reservoir through the first internal blood flow path and to pump blood to the annular heat exchange space; and (d) a second internal blood flow path defined by the pump, the annular heat exchange space, the plurality of hollow fiber membranes, and the blood outlet; and a pump drive motor sized and configured to mountably and detachably receive the pump thereon and to operatively engage and power the pump when the pump is mounted thereon.

2. The blood processing unit of claim 1 wherein the pump further comprises a centrifugal type pump incorporating a rotatable impeller, the rotatable impeller having at least one magnetic body thereon and wherein the pump drive motor further comprises a rotating magnet operative to magnetically engage the at least one magnetic body of the rotatable impeller and to thereby cause rotation of the rotatable impeller.

3. The blood processing unit of claim 1 wherein the blood reservoir further comprises:

an inner reservoir chamber defined by the outer shell;

a microscreen filter element disposed within the inner reservoir chamber, the microscreen filter element being configured to define therewithin an inner blood-receiving compartment having a top end and a bottom end;

a blood inlet tube for passing combined cardiotomy and venous return blood into the inner blood-receiving compartment such that the blood may subsequently pass outwardly through the microscreen filter element;

at least one defoamer element disposed within the inner blood-receiving compartment proximate the top end thereof, the at least one defoamer element containing a chemical defoaming agent to effect defoaming of blood; and a filtered blood outlet port formed in the inner reservoir chamber spaced from the microscreen filter element for communicating outflow of filtered blood from the inner reservoir chamber.

4. The blood processing unit of claim 3 further comprising:

a generally conical baffle structure positioned within the inner blood-receiving compartment for receiving and dispersing blood flowing out of the blood inlet tube.

5. The blood processing unit of claim 1 further comprising:

a video recorder positioned proximate the blood processing unit for recording an image of at least a portion of the blood processing unit; and a monitor mounted on a control console and operative to display the recorded image to an operator stationed at the control console.

6. The blood processing unit of claim 1 wherein the blood reservoir, membrane oxygenator/heat exchanger and pump components are disengagable as a collective unit from the pump drive motor.

7. The blood processing unit of claim 1 wherein the pump comprises a peristaltic pump.

8. The blood processing unit of claim 1 wherein the pump comprises a ventricular type pump.

9. The blood processing unit of claim 1 wherein the pump comprises an axial pump.

10. The blood processing unit of claim 1 wherein the pump drive motor further comprises a reusable drive motor base which is attachable to a support member and mountably and detachably receives the integral structure.

11. The blood processing unit of claim 10 wherein the support member further comprises a vertical pole stand.

12. The blood processing unit of claim 1 further comprising a first internal passageway fluidly connecting the annular heat exchange space with the plurality of hollow fiber membranes.

13. The blood processing unit of claim 12 further comprising an aperture for fluidly connecting the blood reservoir and the first internal blood flow path.

14. The blood processing unit of claim 13 further comprising a second internal passageway fluidly connecting the first internal blood flow path with the annular heat exchange space, wherein blood received by the pump is propelled through the second internal passageway to the annular heat exchange space.

15. The blood processing unit of claim 14 wherein the first internal blood flow path comprises a vertical central tube connecting the aperture with the second internal passageway.

16. The blood processing unit of claim 14 further comprising a blood collection space fluidly connecting the plurality of hollow fiber membranes and the blood outlet.

17. A blood processing unit for extracorporeal blood oxygenation, said blood processing unit being connectable by non-blood transporting connection to a remote control console, the blood processing unit comprising:

an integral structure comprising (a) a blood reservoir, (b) a membrane oxygenator/heat exchanger formed integrally below the blood reservoir and comprising an outer shell, a hollow bore provided therethrough, an annular heat exchange space provided adjacent the outer shell, a plurality of hollow fiber membranes provided between the hollow bore and the annular heat exchange space and in fluid communication with the annular heat exchange space, and a blood outlet disposed in fluid communication with the annular heat exchange space, and (c) a pump disposed between the blood reservoir and the membrane oxygenator/heat exchanger so as to pump blood from the blood reservoir to the plurality of hollow fiber membranes, and including a drive shaft having first and second ends extending through the hollow bore and the first end operatively engaged with the pump;

an internal blood flow path defined by the blood reservoir, the pump, the plurality of hollow fiber membranes, the annular heat exchange space, and the blood outlet; and a pump drive motor operatively engaged with the second end of the drive shaft opposite the first end to rotate the drive shaft and to power the pump.

18. The blood processing unit of claim 17 wherein the pump further comprises a centrifugal type pump incorporating a rotatable impeller.

19. The blood processing unit of claim 17 wherein the blood reservoir further comprises:

an inner reservoir chamber defined by the outer shell;

a microscreen filter element disposed within the inner reservoir chamber, the microscreen filter element being configured to define therewithin an inner blood-receiving compartment having a top end and a bottom end;

a blood inlet tube for passing combined cardiotomy and venous return blood into the inner blood-receiving compartment such that the blood may subsequently pass outwardly through the microscreen filter element;

at least one defoamer element disposed within the inner blood-receiving compartment proximate the top end thereof, the at least one defoamer element containing a chemical defoaming agent to effect defoaming of blood; and a filtered blood outlet port formed in the inner reservoir chamber spaced from the microscreen filter element for communicating outflow of filtered blood from the inner reservoir chamber.

20. The blood processing unit of claim 19 further comprising:

a generally conical baffle structure positioned within the inner blood-receiving compartment for receiving and dispersing blood flowing out of the blood inlet tube.

21. The blood processing unit of claim 17 further comprising:

a video recorder positioned proximate the blood processing unit for recording an image of at least a portion of the blood processing unit; and a monitor mounted on a control console and operative to display the recorded image to an operator stationed at the control console.

22. The blood processing unit of claim 17 wherein the blood reservoir, membrane oxygenator/heat exchanger and pump components are disengagable as a collective unit from the pump drive motor.

23. The blood processing unit of claim 17 wherein the pump comprises a peristaltic pump.

24. The blood processing unit of claim 17 wherein the pump comprises a ventricular type pump.

25. The blood processing unit of claim 17 wherein the pump comprises an axial pump.

26. The blood processing unit of claim 17 wherein the pump drive motor further comprises a reusable drive motor base which is attachable to a support member and mountably and detachably receives the unitary integral structure.

27. The blood processing unit of claim 17 wherein the support member further comprises a vertical pole stand.

28. The blood processing unit of claim 17 further comprising an aperture for fluidly connecting the blood reservoir and the plurality of hollow fiber membranes.

29. The blood processing unit of claim 28 further comprising a first internal passageway fluidly connecting the plurality of hollow fiber membranes with the annular heat exchange space, wherein blood received by the pump is propelled downwardly through the plurality of hollow fiber membranes and subsequently through the first internal passageway and then upwardly through the annular heat exchange space.

30. The blood processing unit of claim 29 further comprising a seal provided within the hollow bore for preventing the downward flow of blood through the hollow bore and to divert the flow of blood to the plurality of hollow fiber membranes.

31. The blood processing unit of claim 30 wherein the pump comprises an axial pump, the axial pump provided with a pump shaft having a lower end engaged with the first end of the drive shaft.

32. A method for processing blood during extracorporeal blood oxygenation, comprising the steps of:

(a) providing a combined blood processing unit having a unitary blood structure comprising (i) a blood reservoir, (ii) a membrane oxygenator/heat exchanger formed integrally below the blood reservoir and comprising an outer shell, a central tube for blood to flow therethrough, an annular heat exchange space provided adjacent the outer shell, a plurality of hollow fiber membranes provided between the central tube and the annular heat exchange space and in fluid communication with the annular heat exchange space, and a blood outlet disposed in fluid communication with the plurality of hollow fiber membranes, and (iii) a pump attached below the membrane oxygenator/heat exchanger and fluidly connected to the blood reservoir and the central tube of the membrane oxygenator/heat exchanger;

(b) delivering venous blood from a patient to the blood reservoir;

(c) pumping blood from the blood reservoir downwardly through the central tube and a first internal passageway and then upwardly through the annular heat exchange space;

(d) passing blood from the annular heat exchange space to the plurality of hollow fiber membranes;
(e) oxygenating the blood at the plurality of hollow fiber membranes; and
(f) returning arterial blood from the plurality of hollow fiber membranes through an outlet to the patient.

33. The method of claim 32 wherein the step of oxygenating the blood includes the step of circulating the blood downwardly through the plurality of hollow fiber membranes.

34. The method of claim 33 further comprising the step of collecting oxygenated blood in a blood collection space.

35. The method of claim 34 wherein the step of passing blood from the annular heat exchange space to the plurality of hollow fiber membranes includes the step of passing the blood through a second internal passageway fluidly connecting the annular heat exchange space and the plurality of hollow fiber membranes.

36. A method for processing blood during extracorporeal blood oxygenation, comprising the steps of:
(a) providing a combined blood processing unit having a unitary blood structure comprising (i) a blood reservoir, (ii) a membrane oxygenator/heat exchanger formed integrally below the blood reservoir and comprising an outer shell, a hollow bore provided therethrough, an annular heat exchange space provided adjacent the outer shell, a plurality of hollow fiber membranes provided between the hollow bore and the annular heat exchange space and in fluid communication with the annular heat exchange space, and a blood outlet disposed in fluid communication with the annular heat exchange space, and (iii) a pump disposed between the blood reservoir and the membrane oxygenator/heat exchanger;
(b) delivering venous blood from a patient to the blood reservoir;
(c) pumping blood from the blood reservoir through an internal aperture to the plurality of hollow fiber membranes;
(d) oxygenating the blood at the plurality of hollow fiber membranes;
(e) passing the oxygenated blood from the plurality of hollow fiber membranes through an internal passageway to the annular heat exchange space; and
(f) returning arterial blood from the annular heat exchange space through an outlet to the patient.

37. The method of claim 36 wherein the step of oxygenating the blood includes the step of circulating the blood downwardly through the plurality of hollow fiber membranes.

* * * * *